(12) United States Patent
Cai et al.

(10) Patent No.: US 7,746,462 B2
(45) Date of Patent: Jun. 29, 2010

(54) INSPECTION SYSTEMS AND METHODS FOR EXTENDING THE DETECTION RANGE OF AN INSPECTION SYSTEM BY FORCING THE PHOTODETECTOR INTO THE NON-LINEAR RANGE

(75) Inventors: Zhongping Cai, Santa Clara, CA (US); Alexander Slobodov, San Jose, CA (US); Anatoly Romanovsky, Palo Alto, CA (US); Christian H. Wolters, Campbell, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 448 days.

(21) Appl. No.: 11/751,293

(22) Filed: May 21, 2007

(65) Prior Publication Data

US 2008/0291454 A1    Nov. 27, 2008

(51) Int. Cl.
*G01N 21/00* (2006.01)
(52) U.S. Cl. .............. 356/237.4; 356/237.1; 356/239.7; 356/445
(58) Field of Classification Search ... 356/237.1–237.6, 356/239.7, 239.8, 442, 445, 239.3
See application file for complete search history.

(56) References Cited

U.S. PATENT DOCUMENTS

| | | | |
|---|---|---|---|
| 3,997,779 A | 12/1976 | Rabl | |
| 6,002,122 A | 12/1999 | Wolf | |
| 6,914,670 B1 | 7/2005 | Almogy et al. | |
| 7,012,683 B2 * | 3/2006 | Wolf et al. | 356/237.2 |
| 2003/0058433 A1 | 3/2003 | Almogy et al. | |
| 2004/0016867 A1 | 1/2004 | Milshtein et al. | |
| 2004/0232835 A1 | 11/2004 | Keller et al. | |
| 2005/0092899 A1 | 5/2005 | Wolf et al. | |
| 2007/0012867 A1 | 1/2007 | Wolters et al. | |
| 2007/0013898 A1 | 1/2007 | Wolters et al. | |
| 2008/0204718 A1 * | 8/2008 | Trainer | 356/73 |

FOREIGN PATENT DOCUMENTS

| | | |
|---|---|---|
| DE | 102004051842 | 12/2005 |
| WO | 2007/011630 | 1/2007 |

OTHER PUBLICATIONS

International Search Report & Written Opinion, PCT/US2008/063541, mailed Sep. 3, 2008.

* cited by examiner

*Primary Examiner*—Gregory J Toatley, Jr.
*Assistant Examiner*—Iyabo S Alli
(74) *Attorney, Agent, or Firm*—Kevin L. Daffer; Daffer McDaniel, LLP

(57) ABSTRACT

An inspection system and method is provided herein for increasing the detection range of the inspection system. According to one embodiment, the inspection system may include a photodetector having a plurality of stages, which are adapted to convert light scattered from a specimen into an output signal, and a voltage divider network coupled for extending the detection range of the photodetector (and thus, the detection range of the inspection system) by saturating at least one of the stages. This forces the photodetector to operate in a non-linear manner. However, measurement inaccuracies are avoided by calibrating the photodetector output to remove any non-linear effects that may be created by intentionally saturating the at least one of the stages. In one example, a table of values may be generated during a calibration phase to convert the photodetector output into an actual amount of scattered light.

25 Claims, 3 Drawing Sheets

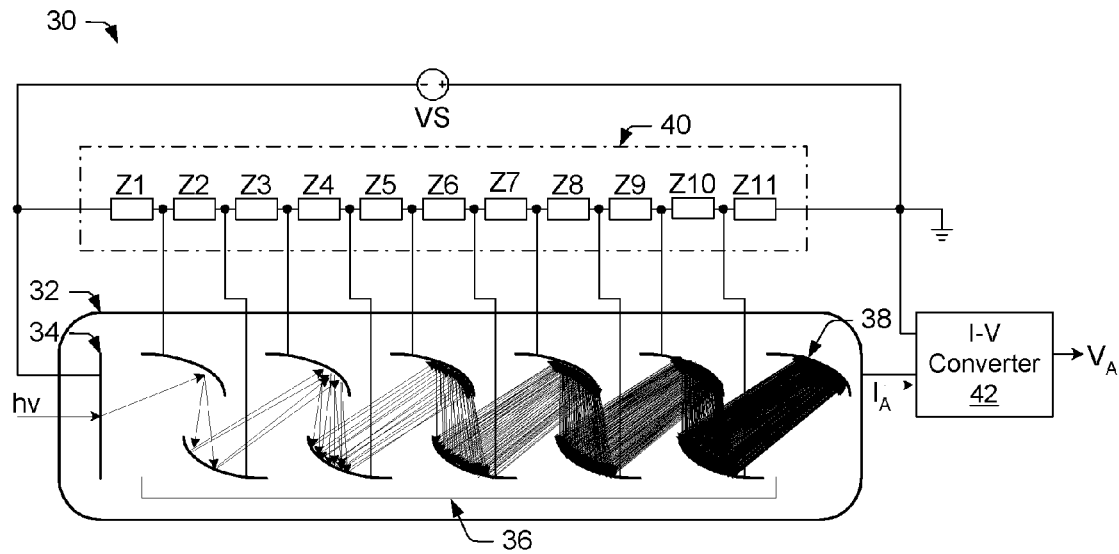
FIG. 2
| STAGE | CATH. | DY1 | DY2 | DY3 | DY4 | DY5 | DY6 | DY7 | DY8 | DY9 | DY10 | AN. |
|---|---|---|---|---|---|---|---|---|---|---|---|---|
| DIST RATIO | 1.0 | 1.0 | 1.0 | 1.0 | 1.0 | 1.0 | 1.0 | 1.0 | 0.1 | 1.2 | 1.2 |
FIG. 3
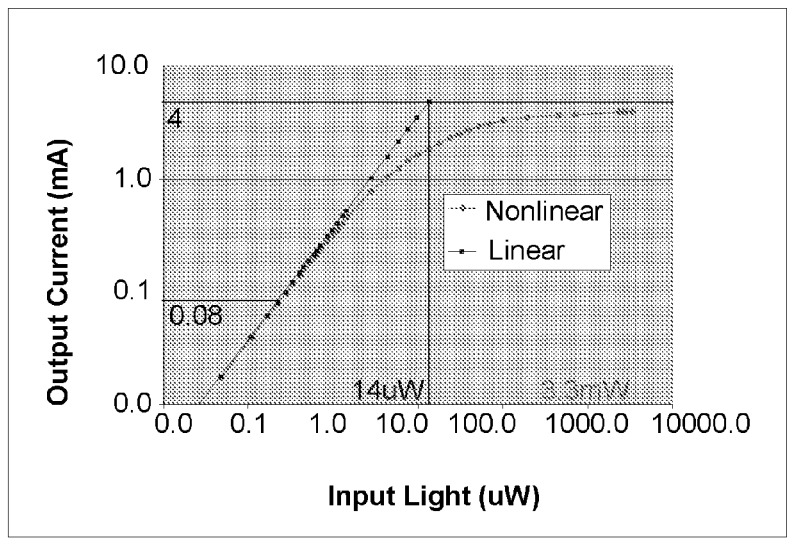
FIG. 4

INSPECTION SYSTEMS AND METHODS FOR EXTENDING THE DETECTION RANGE OF AN INSPECTION SYSTEM BY FORCING THE PHOTODETECTOR INTO THE NON-LINEAR RANGE

BACKGROUND OF THE INVENTION

1. Field of the Invention

This invention relates to systems and methods for extending a detection range of an inspection system used for inspecting a specimen. More specifically, the present invention relates to systems and methods for extending the detection range of an inspection system by forcing the photodetector into the non-linear range.

2. Description of the Related Art

The following descriptions and examples are given as background only.

Fabricating semiconductor devices, such as logic, memory and other integrated circuit devices, typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various steps during a semiconductor manufacturing process to detect defects on wafers to promote higher yield in the manufacturing process, and thus, higher profits. Inspection has always been an important part of semiconductor fabrication. However, as the dimensions of semiconductor devices decrease, inspection becomes even more important to the successful manufacture of acceptable semiconductor devices. For instance, detecting defects of decreasing size has become increasingly necessary, since even relatively small defects may cause unwanted aberrations in the semiconductor device, and in some cases, may cause the device to fail.

Many different types of inspection tools have been developed for the inspection of semiconductor wafers, including optical and E-beam systems. Optical inspection tools may be generally characterized into dark-field and bright-field inspection systems. Dark-field systems typically provide a higher detection range than bright-field systems. For instance, dark-field systems detect the amount of light scattered from the surface of a specimen when an incident beam is supplied to the specimen at a normal or oblique angle. The amount of scattered light detected by the system generally depends on the optical characteristics of the spot under inspection (e.g., the refractive index of the spot), as well as any spatial variations within the spot (e.g., uneven surface topologies). In the case of dark-field inspection, smooth surfaces lead to almost no collection signal, while surfaces with protruding features (such as patterned features or defects) tend to scatter much more strongly (sometimes up to six orders of magnitude or more). On the other hand, bright-field inspection systems direct light to a specimen at a particular angle and measure the amount of light reflected from the surface of the specimen at a similar angle. In contrast to dark-field systems, the detection range of a bright-field system is generally no more than about two orders of magnitude.

Most inspection tools are designed for inspecting either unpatterned or patterned semiconductor wafers, but not both. Since the tools are optimized for inspecting a particular type of wafer, they are generally incapable of inspecting different types of wafers for a number of reasons. For example, most unpatterned wafer inspection tools are configured such that all of the light collected by a lens (or another collector) is directed to a single detector, which generates a single output signal representative of all of the light collected by the lens. Although sufficient for unpatterned wafer inspection, a single detector inspection tool is generally incapable of inspecting patterned wafers.

When used for patterned wafer inspection, the light supplied to a single detector may include light scattered from patterns or features on the patterned wafer in addition to other scattered light (e.g., light scattered from defects). In some cases, the single detector may become saturated, and as a result, may not yield signals that can be analyzed for defect detection. Even if the single detector does not become saturated, the light scattered from patterns or other features on the wafer cannot be separated from the other scattered light thereby hindering, if not preventing, defect detection based on the other scattered light.

For this reason, many patterned wafer inspection tools employ at least two detectors for improved spatial resolution and detection range. An approach of this sort is described by Almogy et al. in U.S. Patent Application Publication No. 2003/0058433, whose disclosure is herein incorporated by reference. Almogy describes an inspection system that utilizes at least two detectors with separate detection channels. One of the detectors is optimized for high resolution, while the other is designed with a high saturation level to improve detection range, typically at the expense of resolution. The light scattered from a specimen is split among the detectors with the addition of various optical components. Although Almogy may improve spatial resolution and detection range, Almogy does so by requiring multiple detectors with additional optics and electronic circuitry, all of which consume additional space, increase complexity, and incur higher cost.

In some cases, one or more of the detectors may become saturated, especially when imaging with a dark-field system. As noted above, dark-field scattering signals obtained from a patterned wafer may vary by six orders of magnitude (or more) due to the variation in surface topology from smooth surface regions (which appear dark) to highly textured regions (which appear bright). It is often difficult, especially with detection systems operating at high data rates, to collect meaningful signals from both the very dark and the very bright areas of the wafer without "on-the-fly" gain adjustment.

"On-the-fly" gain adjustment is another method commonly used to improve spatial resolution and/or detection range. One such method is described by Wolf in U.S. Pat. No. 6,002,122, whose disclosure is herein incorporated by reference. In the method described by Wolf, the output signal from a photomultiplier tube (PMT) is processed by a logarithmic amplifier and gain correction mechanism. The logarithmic amplifier and gain correction mechanism provides a feedback signal to the PMT for adjusting the detector gain "on-the-fly" (e.g., by changing the bias potentials supplied to the dynodes) to account for variations in light supplied to the detector. When larger amounts of light are supplied to the detector, the PMT gain may be reduced to avoid anode saturation, and therefore, extend the detection range. On the other hand, the PMT gain may be increased when smaller amounts of light are supplied to the detector to improve spatial resolution in the low signal range. However, "on-the-fly" gain adjustment tends to increase the level of noise and limit the sensitivity in the low signal range, and requires highly trained personnel to operate the complex and expensive drive electronics.

Therefore, a need remains for improved inspection systems and methods for extending the detection range of a wafer inspection system. Preferably, such improved systems and methods would provide significant detection range extension without the complexity and cost of real-time gain adjustment, as required by Wolf, or the additional detectors, optics and electronic circuitry required by Almogy. In addition, an improved inspection system would extend the detection range without sacrificing sensitivity, resolution or noise performance (especially in the low signal range). In some cases, the improved inspection system may be used for inspecting both patterned and unpatterned wafers.

SUMMARY OF THE INVENTION

The following description of various embodiments of inspection systems and methods is not to be construed in any way as limiting the subject matter of the appended claims.

According to one embodiment, an inspection system is provided herein with improved detection range. In general, the inspection system may include an illumination subsystem configured for directing light to a specimen, and a detection subsystem configured for detecting light scattered from the specimen. In one example, the detection subsystem may include a photodetector having a plurality of stages coupled for receiving and converting the scattered light into an output signal, and a voltage divider network coupled for extending the detection range of the photodetector (and thus, the detection range of the inspection system) by saturating at least one of the stages, thereby forcing the photodetector to operate in the non-linear range.

One or more photodetector stages may be intentionally saturated by supplying a first potential difference between each of a first set of the stages nearest to an input of the photodetector, a second potential difference (substantially higher or lower than the first potential difference) between each of a second set of the stages nearest to an output of the photodetector, and a third potential difference (substantially lower than the first potential difference) between two adjacent stages within the first and second sets. In some cases, the second potential difference may be approximately 50-400% of the first potential difference. In some cases, the third potential difference may be approximately 5-50% of the first potential difference.

The first and second sets of detector stages may be configured to provide a desired amount of detection range and a desired amount of (high end) detection resolution. In some embodiments, the detection range can be maximized by including a majority of the stages in the first set, and relatively few stages in the second set. On the other hand, the (high end) detection resolution may be increased at the expense of detection range by increasing the number of stages within the second set and decreasing the number of stages within the first set.

The inspection system described herein may also include a processor for detecting features, defects or light scattering properties of the specimen. In one embodiment, the processor may calibrate the output signal to remove any non-linear effects created by saturating the photodetector stage(s). For example, the processor may calibrate the output signal by using a pre-computed table of values adapted to correlate the output signal produced by the photodetector to an actual amount of scattered light. The processor may then use the calibrated output signal to detect a feature, defect or light scattering property of the specimen. For example, the actual amount of scattered light obtained from the table of values may be used to determine a size of the detected feature, defect or light scattering property of the specimen.

According to another embodiment, a method is provided herein for increasing a detection range of an inspection system. As noted above, the inspection system may include a photodetector having a plurality of stages, which are adapted to convert light scattered from a specimen into an output signal. In one embodiment, the method may select a potential distribution, which when supplied to the photodetector, intentionally saturates at least one of the detector stages. Next, the method may generate a table of values to remove any non-linear effects created by intentionally saturating the at least one detector stage. The table of values may correlate a range of photodetector output signals to actual amounts of scattered light. As such, the table of values may be used to calibrate a subsequent output signal generated by the photodetector.

In some cases, the step of selecting may include: (i) selecting a first potential difference to be applied between each of a first set of the stages nearest to an input of the photodetector, (ii) selecting a second potential difference, substantially higher or lower than the first potential difference, to be applied between each of a second set of the stages nearest to an output of the photodetector, and (iii) selecting a third potential difference, substantially lower than the first amount, to be applied between two adjacent stages within the first and second sets. In one example, the second potential difference may be approximately 50-400%, while the third potential difference is approximately 5-50% of the first potential difference.

In some cases, the step of selecting may further include selecting a number of the stages to be included within the first set and a number of the stages to be included within the second set. For example, a maximum amount of detection range may be provided, in some embodiments, by including a majority of the stages in the first set and relatively few stages in the second set. On the other hand, the high end detection resolution of the inspection system may be increased at the expense of the detection range by increasing the number of stages within the second set and decreasing the number of stages within the first set.

In some cases, the table of values may be generated by directing light to a test wafer, upon which a known set of particles is formed having known light scattering characteristics. Light scattered from the known set of particles may be detected by the photodetector to obtain the range of photodetector output signals. Next, a numerical fitting and interpolation algorithm may be applied to convert the range of photodetector output signals into the actual amounts of scattered light using the known light scattering characteristics from the test wafer. In one example, the numerical fitting algorithm may be selected from a group comprising linear fitting and interpolation algorithms and polynomial fitting and interpolation algorithms. The table of values may be generated by correlating each photodetector output signal to a respective actual amount of light.

According to another embodiment, a method is provided herein for inspecting a specimen. In one embodiment, the method may include directing light to the specimen and detecting light scattered from the specimen. For example, the step of detecting may include receiving an output signal from a photodetector having a plurality of stages and a potential distribution applied to intentionally saturate at least one of the stages. The step of detecting may also include calibrating the output signal to remove non-linear effects created by intentionally saturating the at least one detector stage. For example, the output signal may be calibrated by comparing the output signal to a table of values correlating a range of output signals to actual amounts of scattered light. In some cases, the table of values may be pre-computed for the photodetector and a particular potential distribution. In some cases, the table of values may be pre-computed for the photodetector and a number of different potential distributions. The calibrated output signal may then be used to detect a feature, defect or light scattering property of the specimen. In one example, the actual amount of scattered light corresponding to the output signal (i.e., the calibrated output signal) may be used to determine a size of the feature, defect or light scattering property of the specimen.

BRIEF DESCRIPTION OF THE DRAWINGS

Other objects and advantages of the invention will become apparent upon reading the following detailed description and upon reference to the accompanying drawings in which:

FIG. 2 is a block diagram of an exemplary circuit included within the detection subsystem of FIG. 1 for detecting the light scattered from the specimen, according to one embodiment of the invention;

FIG. 3 is a table illustrating an exemplary potential distribution that may be applied to the circuit shown in FIG. 2 to increase the detection range of the circuit by operating the circuit in the non-linear range;

FIG. 4 is a graph comparing the non-linear response of the circuit shown in FIGS. 2 and 3 to a conventional detector having a linear response;

Figure 1:
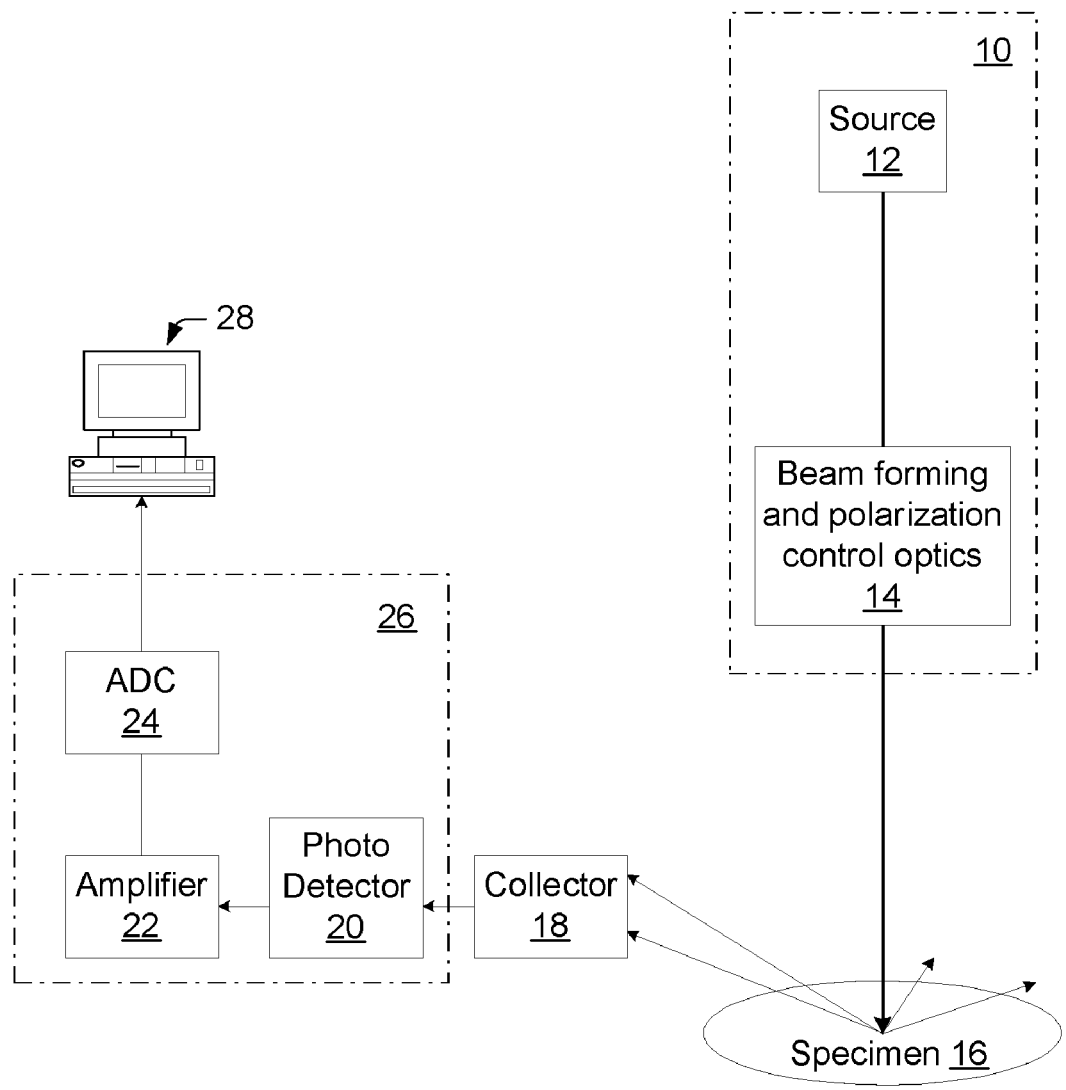
FIG. 1 is a block diagram of an exemplary inspection system including an illumination subsystem for directing light towards a specimen, a detection subsystem for detecting light scattered from the specimen, and a processor for detecting features, defects or light scattering properties of the specimen using the detected light.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

The systems and methods described herein enhance defect detection by using the non-linear range of a detector to extend the overall detection range of a wafer inspection system. Unlike some currently used inspection systems, the inspection system described herein is able to extend the detection range without the expense of sensitivity, complexity, and cost of real-time gain adjustment, and without employing additional detectors, optics and electronic components, all of which undesirably increase space consumption, complexity and cost of the inspection system.

Various embodiments are described herein for an optical inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

In some cases, a wafer may include only the substrate, such as a virgin wafer. Alternatively, a wafer may include one or more layers that may be formed upon a substrate. Examples of such layers may include, but are not limited to, a resist, a dielectric material, and a conductive material. A resist may include a resist that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials, such as "xerogels," and "high-k" dielectric materials, such as tantalum pentoxide. In addition, examples of conductive materials may include, but are not limited to, aluminum, polysilicon, and copper.

One or more layers formed on a wafer may be "patterned" or "unpatterned." For example, a wafer may include a plurality of dies having repeatable pattern features. Formation and processing of such layers of material may ultimately result in completed semiconductor devices. As such, a wafer may include a substrate on which not all layers of a complete semiconductor device have been formed, or a substrate on which all layers of a complete semiconductor device have been formed. The term "semiconductor device" may be used interchangeably herein with the term "integrated circuit." In addition, other devices such as microelectromechanical (MEMS) devices and the like may also be formed on a wafer.

A "reticle" may be a reticle at any stage of a reticle fabrication process, or a completed reticle that may or may not be released for use in a semiconductor fabrication facility. A reticle or a "mask" is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

Turning now to the drawings, it is noted that FIGS. 1-6 are not drawn to scale. In particular, the scale of some of the elements of the figures are greatly exaggerated to emphasize characteristics of the elements. It is also noted that FIGS. 1-6 are not drawn to the same scale. Similar elements shown in more than one figure have been indicated using the same reference numerals.

FIG. 1 illustrates a system that may be used to perform the inspection methods described herein. The system shown in FIG. 1 illustrates a general optical configuration that can be used to inspect a specimen according to the methods described herein. The inspection system includes a dark-field optical subsystem. It will be obvious to one of ordinary skill in the art that the illustrated system may be altered in many ways while still providing the capability to perform the methods described herein. In addition, it will be obvious to one of ordinary skill in the art that the illustrated system may include various additional components that are not shown in FIG. 1 such as a stage, a specimen handler, folding mirrors, polarizers, additional light sources, additional collectors, etc. All such variations are within the scope of the invention described herein.

The system illustrated in FIG. 1 includes an illumination subsystem 10, which is generally configured for directing light to a specimen 16. For example, the illumination subsystem 10 shown in FIG. 1 includes a light source 12. Light source 12 may include, for example, a laser, a diode laser, a helium neon laser, an argon laser, a solid state laser, a diode pumped solid state (DPSS) laser, a xenon arc lamp, a gas discharging lamp, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

The illumination subsystem also includes various beam forming and polarization control optics 14. For example, the illumination subsystem may include various optics for directing and supplying an incident beam of light to specimen 16 with, e.g., a particular spot size. If the light source is configured to emit light of various polarizations, the illumination subsystem may also include one or more polarizing components that may alter the polarization characteristics of the light emitted by the light source. In some cases, the light directed to specimen 16 may be coherent or incoherent. The beam forming and polarization control optics 14 may include a number of components, which are not specifically shown in FIG. 1, such as a beam expander, folding mirrors, focusing lenses, cylindrical lenses, beam splitters, etc.

In some cases, the illumination subsystem 10 may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector is configured for scanning the light beam over the specimen. In some embodiments, the deflector may scan the light beam over the specimen at an approximately constant scanning speed.

As shown in FIG. 1, the illumination subsystem 10 may be configured to direct the beam of light to the specimen at a normal angle of incidence. In this embodiment, the illumination subsystem may not include a deflector since the normal incidence beam of light may be scanned over the specimen by relative motion of the optics with respect to the specimen and/or by relative motion of the specimen with respect to the optics. Alternatively, the illumination subsystem may be configured to direct the beam of light to the specimen at an oblique angle of incidence. The system may also be configured to direct multiple beams of light to the specimen such as an oblique incidence beam of light and a normal incidence beam of light. The multiple beams of light may be directed to the specimen substantially simultaneously or sequentially.

In one embodiment, the inspection system may include a single collection channel as shown in FIG. 1. For example, light scattered from the specimen may be collected by a collector 18, which may be a lens, a compound lens, or any appropriate lens known in the art. Alternatively, collector 18 may be a reflective or partially reflective optical component, such as a mirror. In addition, although one particular collection angle is illustrated in FIG. 1, it is to be understood that the collection channel may be arranged at any appropriate collection angle. The collection angle may vary depending upon, for example, the angle of incidence and/or topographical characteristics of the specimen.

The inspection system also includes a detection subsystem 26 for detecting the light scattered from the specimen and collected by collector 18. As shown in FIG. 1, the detection subsystem may include a detector 20, which generally functions to convert the scattered light into an electrical signal. Detector 20 may include substantially any photodetector known in the art. However, a particular detector may be selected for use within one or more embodiments of the invention based on desired performance characteristics of the detector, the type of specimen to be inspected and/or the configuration of the illumination subsystem. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes and photomultiplier tubes (PMTs) may be used, depending on the amount of light available for inspection and the type of inspection being performed. In at least one preferred embodiment of the invention, a photomultiplier tube is used for detecting light scattered from a specimen to minimize the level of noise in the detector output signal.

The inspection system also includes various electronic components needed for processing the scattered signals detected by detector 20. For example, the system shown in FIG. 1 includes amplifier circuitry 22, analog-to-digital converter (ADC) 24 and processor 28. Amplifier 22 is generally configured to receive output signals from detector 20 and to amplify those output signals by a predetermined amount. ADC 24 converts the amplified signals into a digital format suitable for use within processor 28. In one embodiment, the processor may be coupled directly to ADC 24 by a transmission medium, as shown in FIG. 1. Alternatively, the processor may receive signals from other electronic components coupled to ADC 24. In this manner, the processor may be indirectly coupled to ADC 24 by a transmission medium and any intervening electronic components.

In general, processor 28 is configured for detecting features, defects, or light scattering properties of the specimen using electrical signals obtained from the single collection channel. The signals produced by the single collection channel are representative of the light detected by a single detector (detector 20). The term "single detector" may be used herein to describe a detector having only one sensing area, or possibly several sensing areas (such as found, e.g., in a detector array or multi-anode PMT). Regardless of number, the sensing areas of a single detector are embodied within a single enclosure. In some cases, the inspection system described herein may be used for inspecting patterned, as well as unpatterned specimens. The processor may include any appropriate processor known in the art. In addition, the processor may be configured to use any appropriate defect detection algorithm or method known in the art. For example, the processor may use a die-to-database comparison or a thresholding algorithm to detect defects on the specimen.

The inspection system described herein is able to detect a significantly greater range of features, defects, and light scattering properties of a specimen than other inspection systems, which unnecessarily limit the detection range by avoiding detector saturation. In direct contrast to conventional systems, the inspection system described herein extends the detection range (e.g., about 10 to 300 times, or more) by intentionally saturating the detector. Data restoration is provided by calibrating the detector output to remove any non-linear effects that may be introduced by detector saturation. The use and benefits of detector saturation will now be described in the context of photomultiplier tubes. It is recognized, however, that the general concepts outlined below may be applicable to other types of detectors.

Photomultiplier tubes (PMTs) are often used as detectors when optical signals are dim (i.e., in low-intensity applications). A typical photomultiplier tube consists of a photoemissive cathode (photocathode) followed by focusing electrodes, a plurality of dynodes (forming an electron multiplier) and an anode (forming an electron collector) in a vacuum tube. When light enters the PMT, the photocathode emits photoelectrons into the vacuum. The focusing electrodes direct the photoelectrons toward the electron multiplier where electrons are multiplied by the process of secondary emission. In particular, photoelectrons are accelerated from the photocathode to the first dynode by an electric field. When they strike the dynode, they dislodge additional electrons to amplify the photoelectric signal. These secondary electrons cascade toward the next dynode where they are again amplified. At the end of the dynode chain, the electrons are collected by the anode to generate an electrical output signal in proportion to the amount of light entering the PMT. The output signal produced at the anode is typically large enough to be measured with conventional electronics, such as a transimpedance amplifier followed by an analog-to-digital converter.

The process of secondary emission enables the photomultiplier tube to achieve high current amplification. In other words, a very small photoelectric current from the photocathode can be observed as a large output current from the anode of the photomultiplier tube. The total amount of current amplification (otherwise referred to as detector gain) is the ratio of the anode output current to the photoelectric current from the photocathode. The portion of gain present at each dynode is proportional to the electric potential between that dynode and the previous stage. The total gain of the PMT is the product of the gains from all dynode stages. When a voltage (V) is applied between the cathode and the anode of a photomultiplier tube having (n) dynode stages, the total gain becomes:

$$G(V) \propto V^{\alpha n} \quad \text{EQ. 1}$$

where $\alpha$ is a coefficient (typically in the range of 0.6 to 0.8) determined by the material composition and geometric structure of the dynode.

In some cases, a photomultiplier tube may be operated at a single, predetermined gain. For example, bias voltages may be generated for each of the dynodes by connecting a string of voltage-divider resistors between the cathode, the dynodes, the anode and ground. The resistance, R, is used as a scaling constant and is usually the same for all stages of the photomultiplier tube. A large negative voltage (typically −500 V to −1500 V) is applied to the cathode, and the potential is usually divided up evenly across the dynodes by the voltage-divider resistor chain. Doing so enables each of the dynodes to be maintained at successively less negative potentials, the difference between which establishes the intermediate dynode gain.

The detection range of a photomultiplier tube is limited on the low end by the noise and gain characteristics of the PMT and its amplification circuitry and, on the high end, by the ability of the photomultiplier tube to deliver anode current. Saturation due to space charge effects within the tube, limited bias string power consumption, or the consumable nature of the material coating the cathode and dynodes is generally responsible for limiting the anode current. Saturation could happen at the anode, and sometimes, one or more additional stages (e.g., the cathode or one or more of the dynodes). In most cases, the photomultiplier tube may provide inaccurate results when relatively large amounts of light or high gain cause the anode (and possibly one or more additional stages) to become saturated.

Gain modulation has been used in the past to extend the dynamic range of a photomultiplier tube. Although the total gain of the photomultiplier tube may be altered by changing the voltage applied to the cathode, it is generally not desirable to do so. Therefore, the PMT gain is typically modulated by changing the potential difference supplied to one or more of the detector stages. However, gain modulation is typically used to avoid detector saturation, which distorts the detector output signal by operating the PMT in the non-linear range.

In contrast, the present invention utilizes detector saturation to its advantage. As described in more detail below, the present invention increases the detection range of an inspection system by intentionally saturating at least one of the detector stages (e.g., the anode and possibly one or more of the latter dynode stages). The present invention avoids measurement inaccuracies by calibrating the detector output to remove any non-linear effects introduced by detector saturation.

FIG. 2 illustrates one embodiment of a circuit 30 that may be used for detecting light scattered from a specimen. As such, circuit 30 may be incorporated within the inspection system of FIG. 1 as detector 20. In the embodiment of FIG. 2, circuit 30 includes a photomultiplier tube (PMT) 32 having a cathode 34, a plurality of dynodes 36 and an anode 38. Though shown having 10 dynodes, PMT 32 may include substantially any appropriate number of dynodes, with typical numbers ranging between about 8 and about 20. PMT 32 is also illustrated in FIG. 2 as a head-on photomultiplier tube, and in particular, a linear-focused head-on PMT with a transmission mode photocathode. However, one of ordinary skill in the art would recognize how the inventive aspects described herein may be applied to other types of PMTs. For example, PMT 32 may be alternatively formed in a side-on configuration with a reflection mode photocathode. In addition to the linear-focused PMT shown in FIG. 2, the inventive aspects could be applied to other types of PMTs including, but not limited to, circular-cage type, box-and-grid type, Venetian blind type, and mesh type.

Like conventional PMT circuits, circuit 30 includes a voltage-divider chain 40 with impedance elements (e.g., Z1-Z11) coupled across the cathode, the dynodes and the anode. The impedance elements shown in FIG. 2 may include resistors, capacitors, transistors, diodes or any combination thereof, as is known in the art. When a high negative voltage ($V_S$) is applied to the cathode, the potential is divided up across the dynodes, so that each dynode experiences a specific amount of gain. One manner of dividing the potential is illustrated in FIG. 3 and described in more detail below.

When light (hv) enters the PMT, cathode 34 emits photoelectrons which cascade through dynode chain 36 to produce an amplified photoelectric current ($I_A$) at anode 38. In some cases, the current output from anode 38 may be converted into a voltage ($V_A$) by current-to-voltage converter 42. In one embodiment (not shown), converter 42 may be an operational amplifier with transimpedance ($Z_F$), such that the voltage ($V_A$) generated at the output of the PMT is related to the anode current by:

$$V_A = -I_A * Z_F \qquad \text{EQ. 2}$$

However, converter 42 is not limited to the exemplary embodiment mentioned above. One skilled in the art would recognize that converter 42 may be alternatively configured in other embodiments of the invention. In some cases, the voltage ($V_A$) output from PMT 32 may be supplied to amplification circuitry 22 (FIG. 1) for further processing.

Unlike conventional PMT circuits, voltage divider chain 40 is specifically configured for extending the detection range of the PMT by saturating at least one of the detector stages. In general, one or more stages of the PMT may be intentionally saturated by supplying a first potential difference between each of a first set of the stages nearest to an input of the PMT, a second potential difference (substantially higher or lower than the first potential difference) between each of a second set of the stages nearest to an output of the PMT, and a third potential difference (substantially lower than the first potential difference) between two adjacent stages within the first and second sets. Detector saturation occurs at the adjacent stages (herein referred to as the "saturation stages") by applying a potential difference, which is low enough to cause space charge effects.

Generally speaking, the first and second sets of detector stages may be configured to provide a desired amount of detection range and resolution. In some embodiments, the detection range can be maximized by including a majority of the stages in the first set, and relatively few stages in the second set. On the other hand, the high end detection resolution may be increased at the expense of detection range by increasing the number of stages within the second set and decreasing the number of stages within the first set.

In addition, or alternatively, a desired amount of detection range and resolution may be provided by selecting the appropriate potential differences to be applied between the individual detector stages. At certain stages selected for saturation, lower potential differences can be applied to deepen saturation and widen the detection range at the expense of lower resolution in the high end range. In some embodiments, the potential difference applied between the saturation stages may be approximately 5-50% of the potential difference applied between each of the first set of stages. In some embodiments, the potential difference applied between each of the second set of stages may be approximately 50-400% of the potential difference applied between each of the first set of stages. As described in more detail below, the potential difference applied between the saturation stages can be modified, along with the number of stages included within the second set, to fine tune the detection resolution in the high end range.

In some cases, the number of stages included within the first and second sets may be selected, along with the potential differences applied between stages, to maximize the range of input light that can be safely and accurately detected by the PMT. As described in more detail below, the input light is proportional to the size of the feature, defect or light scattering property of the specimen (hereinafter referred to as a "particle"). Larger particles tend to scatter more light, while smaller particles scatter less light. Therefore, it may be desirable in at least one embodiment of the invention to maximize the range of detectable input light, so as to maximum the range of particle sizes that can be detected during a single measurement operation (e.g., a single wafer scan).

The table shown in FIG. 3 illustrates one embodiment of a voltage biasing scheme (or potential distribution scheme) that may be applied to a 10-stage PMT (e.g., PMT 32 of FIG. 2) for generating an appropriate non-linear response. In the particular example shown in FIG. 3, a potential distribution ratio of 1.0 is applied between the cathode and dynodes DY1-DY8. A significantly lower potential distribution ratio of about 0.1 is applied between dynodes DY8 and DY9 to induce space charge effects and saturation there between. A significantly higher potential distribution ratio of about 1.2 is applied between the anode and the remaining dynodes (DY9 and DY10). As described in more detail below, the lower potential difference applied to the saturation stage reduces the linear range and increases the non-linear range of the PMT output response. The higher potential difference applied after the saturation stage steepens the response curve to increase resolution in the non-linear range.

The graph shown in FIG. 4 compares one embodiment of a non-linearly biased PMT to a conventional linearly biased PMT, which operates primarily in the linear range. In particular, the graph plots PMT output current (expressed in mA) over a range of possible input light values (expressed in µW). As shown in FIG. 4, the conventional PMT is able to detect a very limited input light range (e.g., about 0-14 µW). This is due, in part, to strict conventional adherence to maintaining PMT operation primarily in the linear range. In contrast, the non-linearly biased PMT shown in FIGS. 2 and 3 is able to detect significantly larger input variations (e.g., about 0-3300 µW including a 0-0.2 uW linear range and a 0.2 uW-3300 uW nonlinear range) by operating the PMT in the non-linear range, while keeping the same high gain in the linear range to maintain the same low end resolution and sensitivity (for a given noise level). In the illustrated embodiment, the non-linearly biased PMT is able to detect about 235 times more light than can be detected with a conventional linearly biased PMT.

In some cases, the potential distribution may be modified to steepen the PMT response curve and increase resolution in the non-linear range by including more stages after the saturation stage (i.e., to provide a higher PMT gain). For example, a lower potential difference may be applied between dynodes DY7 and DY8 to saturate stage DY7-DY8, while a higher potential difference is applied between the anode and the remaining dynodes (DY8-DY10). Although doing so would increase the high end resolution of the PMT output signal, such modification would provide less detection range (e.g., about 0-200 µW) than the example shown in FIGS. 2-4. In other cases, the potential distribution could be modified to flatten the PMT response curve in the non-linear range by including fewer stages after the saturation stage (i.e., to provide lower PMT gain). Such modification may be selected to further increase the detection range of the PMT (at the expense of the high end detection resolution).

Measurement inaccuracies are introduced by operating the PMT in the non-linear range. To avoid measurement inaccuracies, the present invention provides a method for calibrating the non-linear output. As described in more detail below, the method may use a test wafer having a known set of particle sizes. Before a product wafer is scanned for defects, the test wafer may be scanned by an inspection system (FIG. 1), which uses a particular detector having a particular potential distribution (e.g., PMT 32 of FIGS. 2 and 3). The test wafer is used to calibrate the detector output by obtaining a non-linear response curve similar to the one shown in FIG. 4. In some cases, the test wafer may include a number of different particle sizes (e.g., about 20-30 different sizes) capable of scattering light over a wide detection range. In some cases, more different particle sizes may be included on the test wafer (e.g., a different size for each possible ADC input) to increase calibration accuracy at the expense of increased calibration complexity and time.

Once a detector output response is obtained (as in FIG. 4), a look-up table may be generated based on the calibration data from the test wafer scan. In one embodiment, linear fitting and interpolation may be applied to different sections of the full output range (including both the linear range and the nonlinear range) to correlate the detector output (e.g., the anode current) to an actual amount of scattered light. The size of the particle may be inferred from the actual amount of scattered light. In this manner, values stored within the look-up table may correlate detector output to particle size. The look-up table may then be used during subsequent measurement operations (e.g., during product wafer scans) to correct the measurement inaccuracies introduced by operating the detector in the non-linear range. For example, a correct particle size may be obtained from the look-up table for a given detector output.

In most cases, calibration is performed by software instructions executed within the processor (e.g., processor 28 of FIG. 1). However, the calibration process is not limited to the particular algorithm described above. In some embodiments, accuracy may be increased by increasing the complexity of the calibration process. For example, a polynomial fitting and interpolation algorithm may be used to calibrate the sections of the nonlinear range, instead of the linear fitting and interpolation method mentioned above. Other algorithms not specifically mentioned herein may also be used. Although such algorithms require more computing time during the calibration process, they may be used to increase data restoration accuracy during subsequent product scans.

Figure 5:
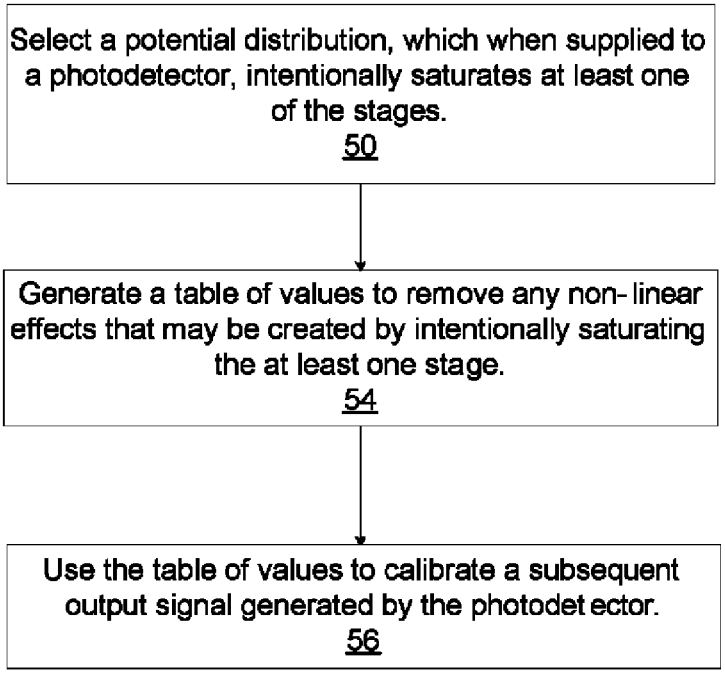
FIG. 5 is a flow chart diagram illustrating one embodiment of a method that may be used for increasing the detection range of an inspection system.

A general method 50 for increasing the detection range of an inspection system, while avoiding measurement inaccuracies, is illustrated in FIG. 5. In one embodiment, the method may begin by selecting a potential distribution 52, that when supplied to the detector, intentionally saturates at least one of the detector stages. Next, a table of values may be generated 54 to remove any non-linear effects created by intentionally saturating the detector stage(s). As noted above, the table of values (or look-up table) may correlate a range of detector output signals to actual amounts of scattered light. Sometime thereafter, the table of values may be used 56 to calibrate a subsequent output signal generated by the detector. In general, method 50 shown in FIG. 5 may be used for calibrating a non-linear detector prior to a product wafer scan.

Figure 6:
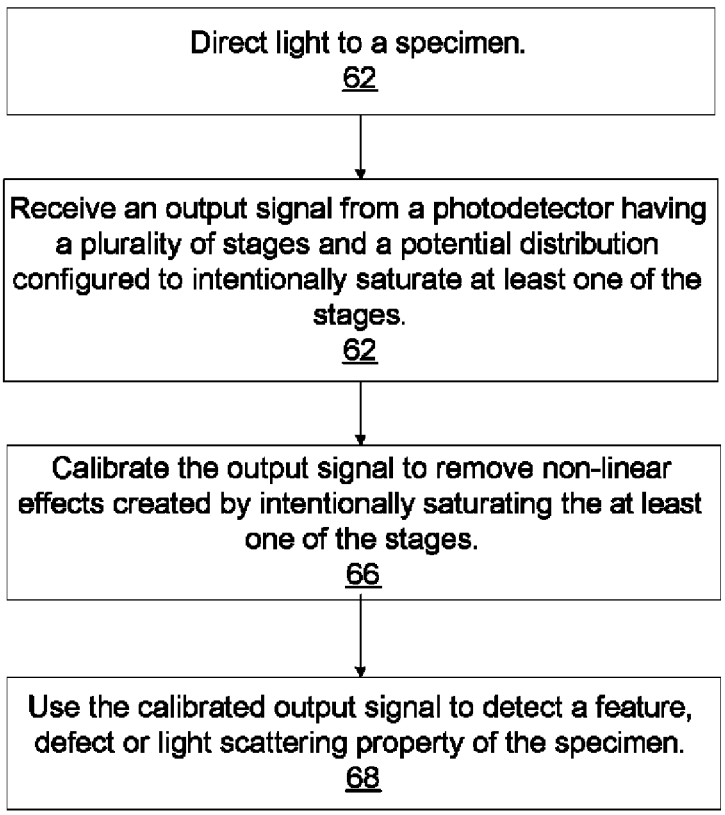
FIG. 6 is a flow chart diagram illustrating one embodiment of a method that may be used for inspecting a specimen.

A general method 60 for inspecting a specimen is illustrated in FIG. 6. In one embodiment, the method may begin by directing light to the specimen 62 and detecting light scattered from the specimen. For example, the step of detecting may include receiving an output signal 64 from a photodetector having a plurality of stages and a potential distribution applied to intentionally saturate at least one of the stages. The step of detecting may also include calibrating the output signal 66 to remove non-linear effects created by intentionally saturating the at least one of the stages. The step of detecting may further include using the calibrated output signal 68 to detect a feature, defect or light scattering property of the specimen. In one example, the calibrated output signal may be used to determine a size of the feature, defect or light scattering property of the specimen. In general, method 60 shown in FIG. 6 may be used for increasing the range of particle sizes detected during a single wafer scan.

Improved inspection systems and methods have been described in accordance with one preferred embodiment of the invention. As noted above, the embodiments illustrated in FIGS. 2-6 may be capable of detecting approximately 235 times more light than conventional detectors, which limit PMT operation to the linear detection range. However, the improved inspection system and method are not limited to only those embodiments specifically illustrated herein. In one alternative embodiment, the detection range may be modified by providing a substantially different potential distribution. For example, and as noted above, the detection range of a PMT may be increased by including fewer stages after the saturation stage (thus, lowering the PMT gain). On the other hand, the detection range may be decreased by including more stages after the saturation stage (thus, increasing the PMT gain).

In another alternative embodiment, the inspection system and method described herein could be combined with techniques described, e.g., in commonly-assigned U.S. application Ser. Nos. 11/181,228 and 11/181,237 to further extend the detection range.

In some cases, the non-linear potential distribution described above may be combined with the PMT detector described in commonly-assigned U.S. application Ser. No. 11/181,228 to increase the detection range further. For example, the previous application illustrates how the detection range can be extended by using a power attenuator subsystem to dynamically alter the power level directed to the specimen based on the scattered light detected from the specimen. In some cases, the power attenuator subsystem may reduce the directed light to a second power level, which is lower than the first power level, if the detected scattered light exceeds a predetermined threshold level. In one example, the two techniques may be combined to extend the detection range by an additional 16 times.

In some cases, the non-linear potential distribution described above may be combined with the PMT detector described in commonly-assigned U.S. application Ser. No. 11/181,237 to further increase the detection range. For example, the previous application illustrates how the amplifier and ADC circuitry of an inspection system can be modified to extend the detection range. In one example, a dual-output amplifier may be used for generating high resolution and low resolution output signals from an output signal provided by the PMT detector described herein (e.g., PMT 32 of FIG. 2). The combination may be used, in some cases, to avoid saturating the amplifier and ADC circuitry by dynamically switching between the high resolution and low resolution output signals during a product wafer scan. This increases the detection range (e.g., by an additional 16 times) and enables more features, defects or light scattering properties of the specimen to be detected by extending the range of particle sizes that can be detected with the two output signals.

It will be appreciated to those skilled in the art having the benefit of this disclosure that this invention is believed to provide an improved inspection system and method for increasing the detection range of the inspection system. For example, the invention provides a photodetector having a plurality of stages and a voltage divider chain configured to extend a detection range of the photodetector by saturating at least one of the stages. More specifically, the invention extends the detection range of the inspection system by intentionally operating the detector in the non-linear range and by providing calibration procedures for compensating for the non-linear effects. In addition to providing superior detection range, the present invention improves upon past techniques by extending the detection range without the expense of sensitivity, complexity and cost of real-time gain adjustment, and without employing additional detectors, optics and electronic components, all of which undesirably increase space consumption, complexity and cost of the inspection system.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention. It is intended, therefore, that the following claims be interpreted to embrace all such modifications and changes and, accordingly, the specification and drawings are to be regarded in an illustrative rather than a restrictive sense.

What is claimed is:

1. An inspection system, comprising:
an illumination subsystem configured for directing light to a specimen;
a detection subsystem configured for detecting light scattered from the specimen, wherein the detection subsystem comprises:
a photodetector having a plurality of stages coupled for receiving and converting the scattered light into an output signal; and
a voltage divider network coupled to extend a detection range of the photodetector by intentionally saturating at least one of the stages used to generate the output signal; and
a processor configured for calibrating the output signal to remove non-linear effects created by saturating the at least one of the stages, and using the calibrated output signal to detect a feature, defect or light scattering property of the specimen.

2. The inspection system as recited in claim 1, wherein the voltage divider network is configured for generating:
a first potential difference between each of a first set of the stages nearest to an input of the photodetector;
a second potential difference, substantially higher or lower than the first potential difference, between each of a second set of the stages nearest to an output of the photodetector; and
a third potential difference, substantially lower than the first potential difference, between two adjacent stages within the first and second sets.

3. The inspection system as recited in claim 2, wherein the second potential difference is selected from a range comprising approximately 50-400% of the first potential difference.

4. The inspection system as recited in claim 2, wherein the third potential difference is selected from a range comprising approximately 5-50% of the first potential difference.

5. The inspection system as recited in claim 2, wherein the first and second sets of stages are configured to provide a desired amount of detection range and a desired amount of detection resolution.

6. The inspection system as recited in claim 5, wherein a maximum amount of detection range is provided by including a majority of the stages in the first set and relatively few stages in the second set.

7. The inspection system as recited in claim 6, wherein the detection resolution is increased at the expense of the detection range by increasing the number of stages within the second set and decreasing the number of stages within the first set.

8. The inspection system as recited in claim 1, wherein the output signal is calibrated by using a pre-computed table of values adapted to correlate the output signal produced by the photodetector to an actual amount of scattered light.

9. The inspection system as recited in claim 8, wherein the actual amount of scattered light is used by the processor to determine a size of the detected feature, defect or light scattering property of the specimen.

10. A method for increasing a detection range of an inspection system comprising a photodetector having a plurality of stages, which are adapted to convert light scattered from a specimen into an output signal, wherein the method comprises:
selecting a potential distribution, which when supplied to the photodetector, intentionally saturates at least one of the stages used to generate the output signal;
generating a table of values correlating a range of photodetector output signals to actual amounts of scattered light to remove non-linear effects created by intentionally saturating the at least one of the stages;
using the table of values to calibrate a subsequent output signal generated by the photodetector.

11. The method as recited in claim 10, wherein the step of selecting comprises:
selecting a first potential difference to be applied between each of a first set of the stages nearest to an input of the photodetector;
selecting a second potential difference, substantially higher or lower than the first potential difference, to be applied between each of a second set of the stages nearest to an output of the photodetector; and
selecting a third potential difference, substantially lower than the first potential difference, to be applied between two adjacent stages within the first and second sets.

12. The method as recited in claim 11, wherein the second potential difference is selected from a range comprising approximately 50-400% of the first potential difference.

13. The method as recited in claim 11, wherein the third potential difference is selected from a range comprising approximately 5-50% of the first potential difference.

14. The method as recited in claim 11, wherein the step of selecting further comprises selecting a number of the stages to be included within the first set and a number of the stages to be included within the second set.

15. The method as recited in claim 14, wherein a maximum amount of detection range is provided by including a majority of the stages in the first set and relatively few stages in the second set.

16. The method as recited in claim 15, wherein a detection resolution of the inspection system is increased at the expense of the detection range by increasing the number of stages within the second set and decreasing the number of stages within the first set.

17. The method as recited in claim 10, wherein the step of generating a table of values comprises:
directing light to a test wafer, upon which a known set of particles is formed having known light scattering characteristics;
detecting light scattered from the known set of particles using the photodetector and the selected potential distribution, wherein the step of detecting comprises obtaining the range of photodetector output signals;

applying a numerical fitting and interpolation algorithm to convert the range of photodetector output signals into the actual amounts of scattered light using the known light scattering characteristics from the test wafer; and generating the table of values by correlating each photodetector output signal to a respective actual amount of light.

18. The method as recited in claim 17, wherein the step of generating a table of values further comprises correlating each photodetector output signal to a respective known light scattering characteristic.

19. The method as recited in claim 17, wherein the known light scattering characteristics comprise a particle size for each of the known set of particles.

20. The method as recited in claim 17, wherein the numerical fitting and interpolation algorithm is selected from a group comprising linear fitting and interpolation algorithms and polynomial fitting and interpolation algorithms.

21. A method for inspecting a specimen, the method comprising:
   directing light to the specimen;
   detecting light scattered from the specimen, wherein said detecting comprises:
      receiving an output signal from a photodetector having a plurality of stages and a potential distribution applied to intentionally saturate at least one of the stages used to generate the output signal;
      calibrating the output signal to remove non-linear effects created by intentionally saturating the at least one of the stages; and
      using the calibrated output signal to detect a feature, defect or light scattering property of the specimen.

22. The method as recited in claim 21, wherein the step of calibrating the output signal comprises comparing the output signal to a table of values correlating a range of output signals to actual amounts of scattered light.

23. The method as recited in claim 22, wherein the table of values is pre-computed for the photodetector and a particular potential distribution.

24. The method as recited in claim 22, wherein the table of values is pre-computed for the photodetector and a number of different potential distributions.

25. The method as recited in claim 22, wherein the step of using the calibrated output signal comprises using the actual amount of scattered light corresponding to the output signal to determine a size of the feature, defect or light scattering property of the specimen.

\* \* \* \* \*